United States Patent
Smith et al.

(10) Patent No.: US 9,739,761 B2
(45) Date of Patent: Aug. 22, 2017

(54) PARTICULATE MATTER FILTER DIAGNOSTIC TECHNIQUES BASED ON EXHAUST GAS ANALYSIS

(71) Applicants: Michael A Smith, Clarkston, MI (US); Kiran Premchand, Lake Orion, MI (US); Homayoun Ahari, Bloomfield Hills, MI (US); Jeffrey P Wuttke, Sterlings Heights, MI (US); Brett Schubring, Macomb, MI (US); Craig L Dimaggio, Troy, MI (US); Michael G Zammit, White Lake, MI (US); Michael T Vincent, Novi, MI (US)

(72) Inventors: Michael A Smith, Clarkston, MI (US); Kiran Premchand, Lake Orion, MI (US); Homayoun Ahari, Bloomfield Hills, MI (US); Jeffrey P Wuttke, Sterlings Heights, MI (US); Brett Schubring, Macomb, MI (US); Craig L Dimaggio, Troy, MI (US); Michael G Zammit, White Lake, MI (US); Michael T Vincent, Novi, MI (US)

(73) Assignee: FCA US LLC, Auburn Hills, MI (US)

( * ) Notice: Subject to any disclaimer, the term of this patent is extended or adjusted under 35 U.S.C. 154(b) by 167 days.

(21) Appl. No.: 14/567,632

(22) Filed: Dec. 11, 2014

(65) Prior Publication Data
US 2016/0169784 A1    Jun. 16, 2016

(51) Int. Cl.
*G01N 15/06* (2006.01)
*G01N 33/00* (2006.01)
(Continued)

(52) U.S. Cl.
CPC ........... *G01N 33/004* (2013.01); *F01N 9/002* (2013.01); *G01M 15/106* (2013.01);
(Continued)

(58) Field of Classification Search
CPC .................................................. G01N 15/0656
(Continued)

(56) References Cited

U.S. PATENT DOCUMENTS

| | | | | |
|---|---|---|---|---|
| 3,699,683 A | * | 10/1972 | Tourtellotte | B01D 53/944 422/172 |
| 5,964,089 A | * | 10/1999 | Murphy | B01D 53/90 60/274 |

(Continued)

OTHER PUBLICATIONS

Bischof, C. et al., "Advanced Particulate Filter Technologies for Direct Injection Gasoline Engine Applications", Corning, DEER Conference, Oct. 16-19, 2012, 12 pages.

(Continued)

*Primary Examiner* — Clayton E LaBalle
*Assistant Examiner* — Kevin Butler
(74) *Attorney, Agent, or Firm* — Ralph E. Smith

(57) ABSTRACT

A diagnostic system and method for diagnosing the performance of a particulate matter (PM) filter of an exhaust system each involve receiving, by a controller from at least one sensor, a gas component measurement of exhaust gas flowing through the exhaust system and the PM filter. The controller calculates a conversion efficiency of the gas component by the PM filter and compares the calculated conversion efficiency to a predetermined conversion efficiency threshold indicative of an expected conversion efficiency of a flow-through catalyst. The controller then determines whether the PM filter is cracked or damaged based on the comparison between the calculated conversion efficiency and the predetermined conversion efficiency threshold.

19 Claims, 3 Drawing Sheets

(51) Int. Cl.
*F01N 9/00* (2006.01)
*G01M 15/10* (2006.01)
*G01N 1/38* (2006.01)
*F02B 3/06* (2006.01)
*G01N 1/22* (2006.01)
*G01N 1/24* (2006.01)

(52) U.S. Cl.
CPC ............ *G01N 33/0037* (2013.01); *F02B 3/06* (2013.01); *G01N 1/2205* (2013.01); *G01N 1/24* (2013.01); *G01N 1/38* (2013.01); *G01N 15/0656* (2013.01)

(58) Field of Classification Search
USPC .......................................................... 73/23.33
See application file for complete search history.

(56) References Cited

U.S. PATENT DOCUMENTS

| | | | | |
|---|---|---|---|---|
| 5,974,786 | A * | 11/1999 | Kluzner ................ | F01N 11/007 123/691 |
| 6,499,293 | B1 * | 12/2002 | Surnilla ................ | F01N 3/0814 60/274 |
| 6,948,475 | B1 * | 9/2005 | Wong ..................... | F02B 43/00 123/299 |
| 7,396,389 | B2 * | 7/2008 | Kariya ................... | B01D 46/2418 55/282.2 |
| 7,741,127 | B2 * | 6/2010 | Johnston Bartley .... | F01N 3/021 436/155 |
| 8,468,799 | B2 * | 6/2013 | Post ...................... | F02D 41/0007 60/274 |
| 2003/0140629 | A1 * | 7/2003 | Shirakawa ............ | F02D 35/025 60/600 |
| 2003/0167756 | A1 * | 9/2003 | Szymkowicz .......... | F01N 3/023 60/289 |
| 2004/0116285 | A1 * | 6/2004 | Huang ................... | B01D 53/864 502/325 |
| 2005/0042151 | A1 * | 2/2005 | Alward ................. | B01D 39/2082 422/177 |
| 2008/0264036 | A1 * | 10/2008 | Bellovary ................ | F01N 3/00 60/274 |
| 2009/0044515 | A1 * | 2/2009 | Lu ........................... | F02D 23/02 60/277 |
| 2009/0145111 | A1 * | 6/2009 | Takahashi ............. | B01D 53/944 60/277 |
| 2010/0307339 | A1 * | 12/2010 | Tadrous ............... | B01D 46/0063 95/280 |
| 2010/0308849 | A1 * | 12/2010 | Bouteiller ............. | F01N 3/0222 324/700 |
| 2011/0126529 | A1 * | 6/2011 | Park ....................... | F01N 3/2066 60/303 |
| 2011/0200505 | A1 * | 8/2011 | Cavataio ............... | B01D 53/9418 423/213.2 |
| 2011/0232362 | A1 * | 9/2011 | Thiagarajan ........ | B01D 46/0086 73/23.33 |
| 2012/0031083 | A1 * | 2/2012 | Minami ................. | B01D 53/9477 60/297 |
| 2012/0279206 | A1 * | 11/2012 | Geyer ..................... | F01N 3/0231 60/287 |
| 2013/0318948 | A1 * | 12/2013 | Van Marion ........ | F02D 41/1466 60/277 |
| 2014/0223998 | A1 * | 8/2014 | Yamakawa ............ | F01N 9/002 73/38 |
| 2016/0169784 | A1 * | 6/2016 | Smith .................... | F01N 9/002 73/23.33 |

OTHER PUBLICATIONS

Blakeman, Dr. Phil, "Catalyzed Exhaust Filters: Future directions", Johnson Matthey Catalysts, CLEERS, Apr. 2013, 37 pages.
Surve, Pranati R., "Diesel Particulate Filter Diagnostics Using Correlation and Spectral Analysis", Purdue University, ECE Maters Theses, Jul. 25, 2008, 105 pages.

\* cited by examiner

PARTICULATE MATTER FILTER DIAGNOSTIC TECHNIQUES BASED ON EXHAUST GAS ANALYSIS

FIELD

The present application relates generally to vehicle exhaust systems and, more particularly, to particulate matter filter diagnostic techniques based on exhaust gas analysis.

BACKGROUND

Engines combust a mixture of air and fuel to drive pistons and generate drive torque. Exhaust gas resulting from combustion is treated by an exhaust system before being released into the atmosphere. Example components of the exhaust system include catalysts and particulate matter (PM) filters. Catalysts chemically convert portions of the exhaust gas, and PM filters trap PM in the exhaust gas. Once a PM filter is has reached a maximum storage capacity, it is regenerated by burning the trapped PM at a high temperature. The stress on the PM filter could cause it to crack, which could decrease exhaust system performance and thus increases emissions, Conventional diagnostic systems for a cracked PM filter utilize a PM or particulate number (PN) sensor. These sensors, however, are expensive and thus increase vehicle costs. Therefore, while such diagnostic systems work for their intended purpose, there remains a need for improvement in the relevant art.

SUMMARY

In accordance with an aspect of the invention, a diagnostic system for a particulate matter (PM) filter of an exhaust system is provided. In one exemplary implementation, the diagnostic system includes at least one gas sensor configured to measure a gas component of exhaust gas flowing through the exhaust system and the PM filter, and a controller configured to perform a diagnostic technique for the PM filter. In one exemplary implementation, the controller is configured to calculate a conversion efficiency of the gas component by the PM filter, compare the calculated conversion efficiency to a predetermined conversion efficiency threshold indicative of an expected conversion efficiency of a flowthrough catalyst, and determine whether the PM filter is cracked or damaged based on the comparison between the calculated conversion efficiency and the predetermined conversion efficiency threshold.

In accordance with an aspect of the invention, a method for diagnosing the performance of a PM filter of an exhaust system is provided. In one exemplary implementation, the method includes receiving, by a controller from at least one sensor, measurements of a gas component of exhaust gas flowing through the exhaust system and the PM filter. A conversion efficiency of the gas component by the PM filter is then calculated and the calculated conversion efficiency is compared to a predetermined conversion efficiency threshold indicative of an expected conversion efficiency of a flow-through catalyst. A determination is then made as to whether the PM filter is cracked or damaged based on the comparison between the calculated conversion efficiency and the predetermined conversion efficiency threshold.

In some implementations, the controller is configured to calculate the conversion efficiency of the gas component by the PM filter in response to detecting a kinetic operating condition for the PM filter. In some implementations, the kinetic operating condition for the PM filter includes an exhaust gas temperature range where conversion of the gas component by the PM filter begins to occur.

In some implementations, the diagnostic system further comprises at least one pressure sensor configured to measure an exhaust gas pressure drop across the PM filter, and the controller is further configured to compare the exhaust gas pressure drop to a predetermined pressure drop threshold indicative of an expected exhaust gas pressure drop across a flow-through catalyst, and to determine whether the PM filter is cracked or damaged based on the comparison between the exhaust gas pressure drop and the predetermined pressure drop threshold.

In some implementations, the at least one gas sensor includes an upstream sensor and a downstream sensor positioned upstream and downstream, respectively, of the PM filter or a midbed sensor positioned at or near a middle of the PM filter, and the at least one pressure sensor includes an upstream pressure sensor and a downstream pressure sensor positioned upstream and downstream, respectively, of the PM filter.

In some implementations, the gas component includes carbon monoxide (CO), and wherein the at least one gas sensor includes a sensor configured to measure exhaust gas concentration. In some implementations, the gas component includes hydrocarbons (HC) and, in some implementations, the at least one gas sensor includes a sensor configured to measure exhaust gas temperature. In some implementations, the at least one gas component includes nitrogen oxides (NOx) and, in some implementations, the at least one gas sensor includes a sensor configured to measure at least one of exhaust gas NOx concentration and exhaust gas ammonia (NH3) concentration.

Further areas of applicability of the teachings of the present disclosure will become apparent from the detailed description, claims and the drawings provided hereinafter, wherein like reference numerals refer to like features throughout the several views of the drawings. It should be understood that the detailed description, including disclosed embodiments and drawings referenced therein, are merely exemplary in nature intended for purposes of illustration only and are not intended to limit the scope of the present disclosure, its application or uses. Thus, variations that do not depart from the essence of the present disclosure are intended to be within the scope of the present disclosure.

DESCRIPTION

As previously discussed, there remains a need for more cost-effective diagnostic systems/methods for detecting cracked or otherwise reduced performance particulate matter (PM) filters. Accordingly, PM filter diagnostic techniques based on exhaust gas analysis are presented. In one exemplary implementation, these diagnostic techniques utilize existing sensors in the exhaust system and do not require a PM or particulate number (PN) sensor, which is expensive and thus increases vehicle costs. In one exemplary implementation, the diagnostic techniques involve measuring gas component(s) of an exhaust gas and calculating a conversion efficiency of the gas component(s) by a PM filter (e.g., upstream vs. downstream). Based on a comparison of the conversion efficiency to a threshold, a determination is made whether the PM filter is acting as a wall flow device, which is indicative of a functional PM filter, or as a flow-through device (e.g., a catalyst or catalytic converter), which is indicative of a cracked PM filter because less PM is trapped and more gas molecules are converted. In one exemplary implementation, a PM filter pressure drop is also used in this determination.

Figure 1:
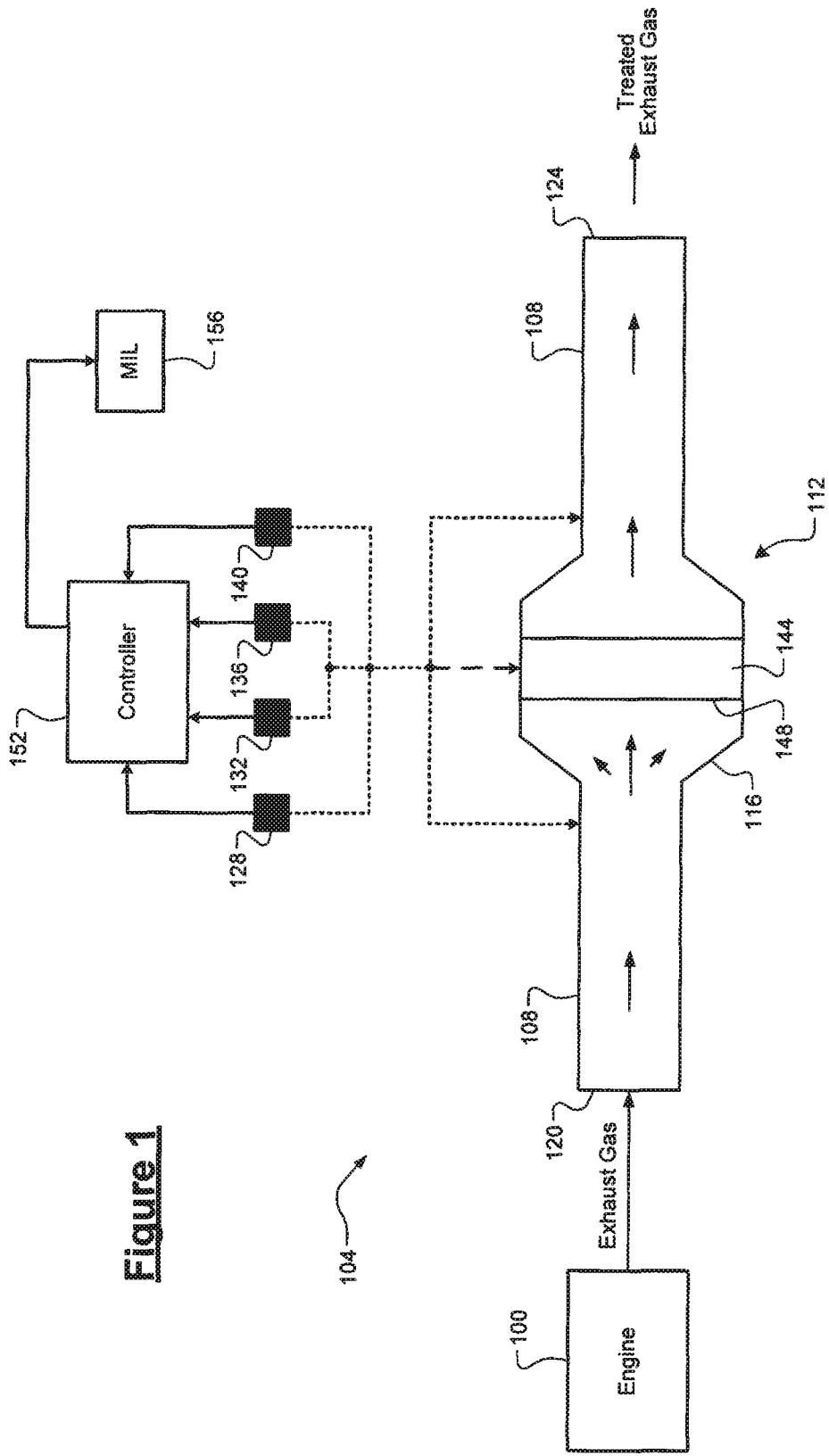
FIG. 1 is an example diagram of an exhaust system according to the principles of the present disclosure.

Referring now to FIG. 1, an example diagram of a combustion after-treatment system or exhaust system 104 is illustrated. The exhaust system 104 is configured to receive and treat exhaust gas produced by an engine 100. Examples of the engine 100 include a gasoline engine and a diesel engine. The engine 100 generates the exhaust gas as a byproduct of air/fuel combustion. The exhaust gas includes various gas components as well as PM. Examples of the gas components include carbon monoxide (GO), hydrocarbons (HG), and nitrogen oxides (NOx). The terms "particulate matter" or "PM" refer to any soot, ash, or other particulates in the exhaust gas. The exhaust system 104 is configured to trap the PM contained in the exhaust gas. The exhaust system 104 includes an exhaust pipe 108 and a PM filter 112. In one exemplary implementation, the PM filter 112 is disposed within a housing 116. The exhaust pipe 108 defines an inlet 120 that receives the exhaust gas and an outlet 124 that releases the treated exhaust gas into the atmosphere.

The exhaust system 104 also includes one or more oxygen sensors 128, one or more temperature sensors 132, and one or more NOx or ammonia ($NH_3$) sensors 136 configured to measure exhaust gas temperature, oxygen concentration, and NOx or $NH_3$ concentrations, respectively. In one exemplary implementation, the exhaust system 104 includes sensors 128, 132, 136 each configured to measure at points upstream and downstream from the PM filter 112. In one implementation, the sensors 128, 132 and 136 are positioned adjacent the PM filter 112. In another exemplary implementation, the sensors 128, 132, 136 are each midbed sensors configured to capture measurements at or near a middle of the PM filter 112. For example, these midbed sensor configurations could be used to obtain partial measurements or estimations of gas component conversion efficiencies.

The exhaust system 104 optionally includes one or more pressure sensors 140 configured to measure exhaust gas pressure, such as at points upstream and downstream from the PM filter 112 (e.g., a pressure drop across the PM filter 112). In one exemplary implementation, the one or more pressure sensors are positioned adjacent the PM filter 112. The exhaust system 104 optionally includes other exhaust treatment components, such as an oxidation catalyst, a selective catalytic reduction (SCR) catalyst, and/or a three-way catalyst (TWC) or catalytic converter (not shown).

These optional other components are configured to decrease or eliminate gas emissions (CO, HC, NOx, etc.). Unlike these other catalysts or catalytic converters that are "flow-through" devices, the PM filter 112 is a "wall flow" device that retains or traps particulate matter by forcing the exhaust gas to flow through or along walls of the PM filter 112. The PM filter 112 includes a filter material 144 arranged in a suitable configuration for trapping PM in the exhaust gas, such as having alternate plugged channels. Examples of the filler material 144 include cordierite, silicon carbide (SiC), ceramic fibers, and metal fibers. Exhaust gas is forced through the filler material 144 while PM is trapped and accumulates on a face 148 of the filler material 144. Once the amount of accumulated PM in the PM filter 112 reaches a critical or predetermined threshold, the PM filter 112 could be regenerated or replaced (e.g., a single-use PM filter).

Regeneration involves increasing a temperature of the exhaust gas to a critical or predetermined temperature that causes the accumulated PM to burn off, thereby clearing or "regenerating" the PM filter 112. As previously discussed, damage to and/or cracking of the PM filter 112 could occur, such as due to high temperature/stress on the PM filter 112 during operation (e.g., during regeneration). Specifically, this cracking could occur in the filter material 144 of the PM filter 112. Therefore, a crack in the PM filter 112 could be determined by detecting that the PM filter 112 is behaving like a flow-through device instead of a wall flow device. A controller 152 is configured to control operation of the exhaust system 104, including monitoring measurements from sensors 128, 132, 136, and 140. The controller 152 is further configured to detect the cracking of the PM filter 112, which is discussed in greater detail below. When a cracked PM filter is detected, the controller 152 is configured to generate a malfunction output, such as actuating a malfunction indicator lamp (MIL) 156.

Figure 2:
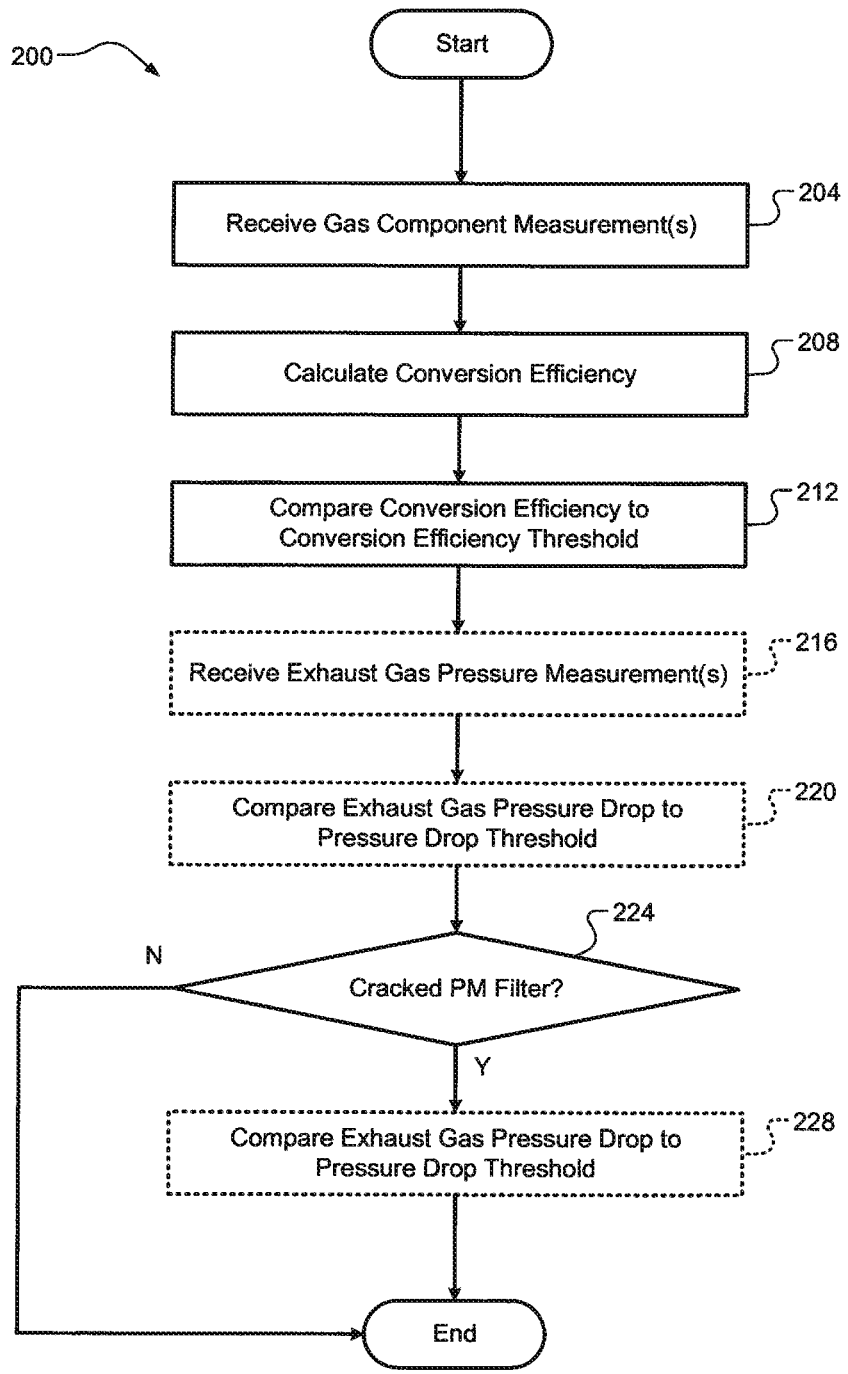
FIG. 2 is an example flow diagram of a particulate matter (PM) filter diagnostic method according to the principles of the present disclosure.

Referring now to FIG. 2, an example flow diagram of a PM filter diagnostic method 200 is illustrated. At 204, the controller 152 receives, from at least one of the sensors 128, 132, 136, measurements of at least one gas component of an exhaust gas flowing through the exhaust system 104 comprising the PM filter 112. Examples of the gas components include CO, HC, oxygen (02) and NOx. For example, exhaust gas CO concentration could be determined based on exhaust gas oxygen concentration measurements, exhaust gas HC concentration could be determined based on exhaust gas temperature measurements, and exhaust gas NOx concentration could be determined based on exhaust gas NOx or $NH_3$ measurements.

At 208, the controller 152 calculates a conversion efficiency of the at least one gas component by the PM filter 112. In other words, the controller 152 determines a degree by which the PM filter 112 is decreasing each gas component (e.g., upstream vs. downstream). At 212, the controller 152 compares the conversion efficiency to a conversion efficiency threshold indicative of an expected conversion efficiency of a flow-through catalyst. This conversion efficiency threshold could be predetermined, such as based on test data. It will be appreciated, however, that this conversion efficiency threshold could also be updated or modified over time. Optionally at 216, the controller 152 receives, from the one or more pressure sensors 140, measurements of exhaust gas pressure, which are indicative of an exhaust pressure drop across the PM filter 112. Optionally at 220, the controller 152 compares the exhaust gas pressure drop to a predetermined pressure drop threshold. In one exemplary implementation, the one or more pressure sensors 140 are positioned adjacent the PM filter 112.

At 224, the controller 152 determines whether the PM filter is cracked or otherwise damaged based on the comparison between the calculated conversion efficiency and the conversion efficiency threshold. Optionally, the controller 152 could perform this determination at 152 further based on the comparison between the exhaust gas pressure drop and the pressure drop threshold. When the conversion efficiency is greater than the conversion efficiency threshold, the controller 152 determines that the PM filter 112 is cracked or otherwise damaged and the method 200 optionally proceeds to 228, ends, or returns to 204. When the conversion efficiency is less than the conversion efficiency threshold, the controller 152 determines that the PM filter 112 is not cracked or is otherwise performing within normal or expected operating parameters, and the method 200 ends or returns to 204. Optionally at 228, the controller 152 generates a malfunction output (e.g., actuating MIL 156) and then the method 200 ends or returns to 204.

Figure 3A:
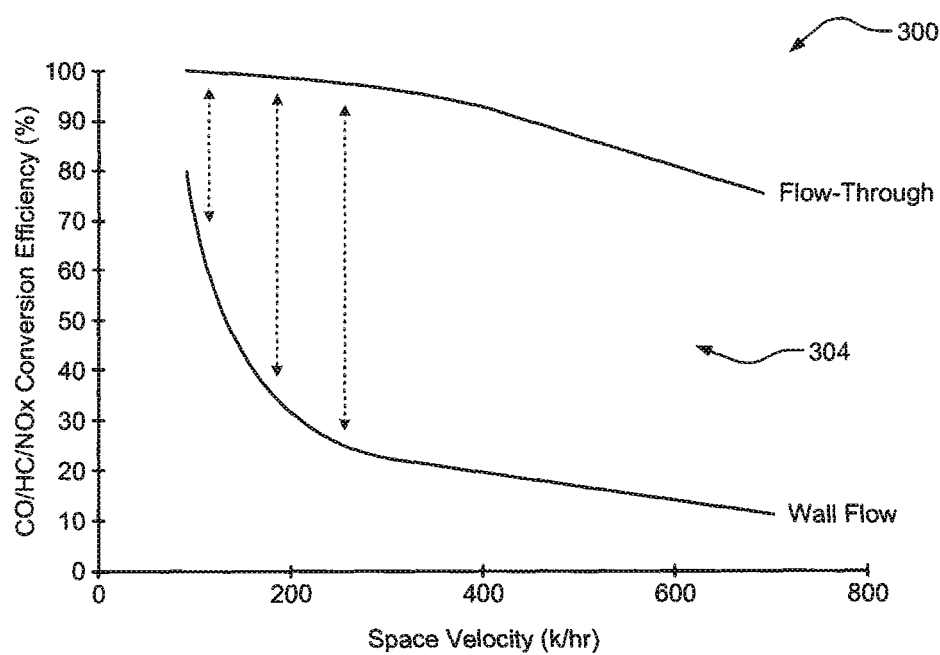
FIGS. 3A and 3B are example graphs of conversion efficiencies for both an example wall flow device and an example flow-through device at a kinetic operating condition and a high temperature condition, respectively, according to the principles of the present disclosure.
Figure 3B:
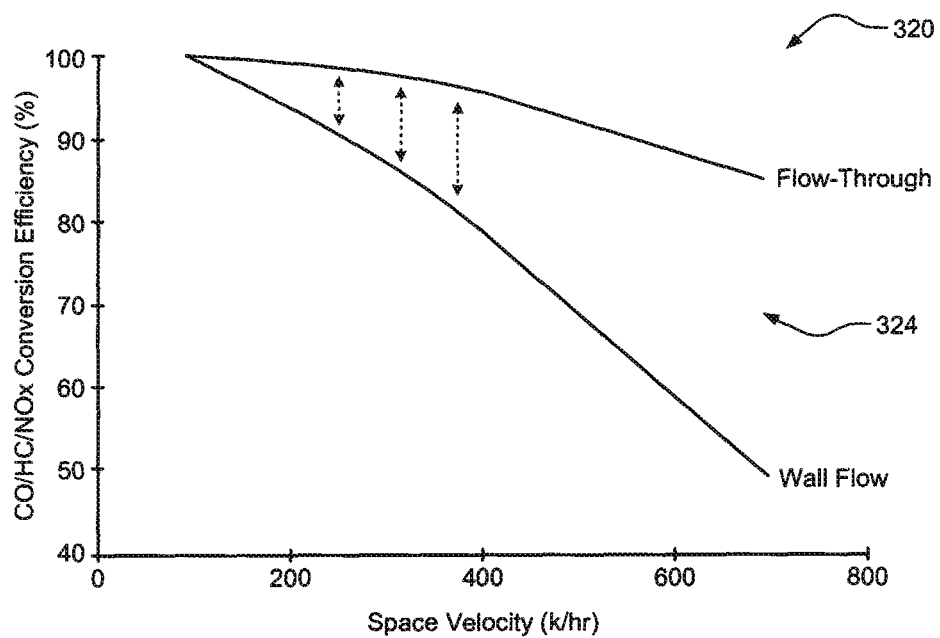

Referring now to FIGS. 3A and 3B, example graphs 300, 320 illustrate conversion efficiencies for both an example wall flow device (e.g., the PM filter 112) and an example flow-through device (e.g., a catalyst or catalytic converter) at a kinetic operating condition and a high temperature condition, respectively. Each graph plots conversion efficiency of at least one gas component (e.g., any combination of CO, HC, and NOx) versus space velocity (e.g., exhaust gas flow rate vs. volume). In FIG. 3A, there is a very large gap between the conversion efficiencies of the example wall flow device and the example flow-through device at the kinetic operating condition, which is also referred to as a mid-level temperature operating condition. This kinetic operating condition represents a point where chemical reactions of the gas component(s) of the exhaust gas begin to occur.

In contrast, in FIG. 3B there is a very small gap between the conversion efficiencies of the example wall flow device and the example flow-through device at a high temperature operating condition that is greater than the kinetic operating condition. Because the conversion efficiency threshold is selected at point(s) between the wall flow device and the flow-through device, a larger gap between expected behavior of a wall flow device and expected behavior of a flowthrough device is desirable. Therefore, calculating the conversion efficiency of the PM filter 112 at the kinetic operating condition could provide more accurate and/or robust results because there is a greater distinction between the expected wall flow device behavior and the expected flow-through device behavior. Thus, the controller 152 could detect this kinetic operating condition (e.g., a specific exhaust gas temperature range) as a precondition to performing the diagnostic technique of the present disclosure.

It should be understood that the mixing and matching of features, elements, methodologies and/or functions between various examples may be expressly contemplated herein so that one skilled in the art would appreciate from the present teachings that features, elements and/or functions of one example may be incorporated into another example as appropriate, unless described otherwise above.

What is claimed is:

1. A diagnostic system for a particulate matter (PM) filter of an exhaust system, the diagnostic system comprising:
    at least one gas sensor configured to measure a gas component of exhaust gas flowing through the exhaust system and the PM filter; and
    a controller configured to:
        calculate a conversion efficiency of the gas component by the PM filter;
        compare the conversion efficiency to a predetermined conversion efficiency threshold indicative of an expected conversion efficiency of a flow-through catalyst; and
        determine whether the PM filter is cracked or damaged based on the comparison between the calculated conversion efficiency and the predetermined conversion efficiency threshold.

2. The diagnostic system of claim 1, wherein the controller is configured to calculate the conversion efficiency of the gas component by the PM filter in response to detecting a kinetic operating condition for the PM filter.

3. The diagnostic system of claim 2, wherein the kinetic operating condition for the PM filter includes an exhaust gas temperature range where conversion of the gas component by the PM filter begins to occur.

4. The diagnostic system of claim 1, further comprising at least one pressure sensor configured to measure an exhaust gas pressure drop across the PM filter, wherein the controller is further configured to:
    compare the exhaust gas pressure drop to a predetermined pressure drop threshold indicative of an expected exhaust gas pressure drop across a flow-through catalyst; and
    determine whether the PM filter is cracked or damaged based on the comparison between the exhaust gas pressure drop and the predetermined pressure drop threshold.

5. The diagnostic system of claim 4, wherein the at least one gas sensor includes an upstream sensor and a downstream sensor positioned upstream and downstream, respectively, of the PM filter or a midbed sensor positioned at or near a middle of the PM filter, and wherein the at least one pressure sensor includes an upstream pressure sensor and a downstream pressure sensor positioned upstream and downstream, respectively, of the PM filter.

6. The diagnostic system of claim 1, wherein the gas component includes carbon monoxide (CO), and wherein the at least one gas sensor includes a sensor configured to measure exhaust gas concentration.

7. The diagnostic system of claim 1, wherein the gas component includes hydrocarbons (HC).

8. The diagnostic system of claim 1, wherein the at least one gas sensor includes a sensor configured to measure exhaust gas temperature.

9. The diagnostic system of claim 1, wherein the gas component includes nitrogen oxides (NOx).

10. The diagnostic system of claim 9, wherein the at least one gas sensor includes a sensor configured to measure at least one of exhaust gas NOx concentration and exhaust gas ammonia ($NH_3$) concentration.

11. A method for diagnosing the performance of a particulate matter (PM) filter of an exhaust system, the method comprising:
    receiving, by a controller from at least one sensor, measurements of a gas component of exhaust gas flowing through the exhaust system and the PM filter;
    calculating, by the controller, a conversion efficiency of the gas component by the PM filter;
    comparing, by the controller, the conversion efficiency to a predetermined conversion efficiency threshold indicative of an expected conversion efficiency of a flow-through catalyst; and
    determining, by the controller, whether the PM filter is cracked or damaged based on the comparison between the calculated conversion efficiency and the predetermined conversion efficiency threshold.

12. The method of claim 11, further comprising calculating the conversion efficiency in response to detecting a kinetic operating condition for the PM filter, wherein the kinetic operating condition for the PM filter includes an exhaust gas temperature range where conversion of the gas component by the PM filter begins to occur.

13. The method of claim 11, further comprising:
    receiving, by the controller from at least one pressure sensor, an exhaust gas pressure drop across the PM filter;

comparing, by the controller, the exhaust gas pressure drop to a predetermined pressure drop threshold indicative of an expected exhaust gas pressure drop across a flow-through catalyst; and determining, by the controller, whether the PM filter is cracked or damaged based on the comparison between the exhaust gas pressure drop and the predetermined pressure drop threshold.

14. The method of claim 13, wherein the at least one gas sensor includes an upstream sensor and a downstream sensor positioned upstream and downstream, respectively, of the PM filter or a midbed sensor positioned at or near a middle of the PM filter, and wherein the at least one pressure sensor includes an upstream pressure sensor and a downstream pressure sensor positioned upstream and downstream, respectively, of the PM filter.

15. The method of claim 11, wherein the gas component includes carbon monoxide (CO), and wherein the at least one gas sensor includes a sensor configured to measure exhaust gas concentration.

16. The method of claim 11, wherein the gas component includes hydrocarbons (HC).

17. The method of claim 11, wherein the at least one sensor includes a sensor configured to measure exhaust gas temperature.

18. The method of claim 11, wherein the gas component includes nitrogen oxides (NOx).

19. The method of claim 18, wherein the at least one sensor includes a sensor configured to measure at least one of exhaust gas NOx concentration and exhaust gas ammonia ($NH_3$) concentration.

* * * * *